United States Patent
Kobayashi et al.

(10) Patent No.: US 8,394,248 B2
(45) Date of Patent: Mar. 12, 2013

(54) GAS SENSOR CONTROL DEVICE AND NITROGEN OXIDE CONCENTRATION DETECTION METHOD

(75) Inventors: Akihiro Kobayashi, Nisshin (JP); Takayuki Sumi, Nagoya (JP); Yasuhiro Ishiguro, Komaki (JP); Satoru Abe, Iwakura (JP)

(73) Assignee: NGK Spark Plug Co., Ltd., Aichi (JP)

( * ) Notice: Subject to any disclaimer, the term of this patent is extended or adjusted under 35 U.S.C. 154(b) by 501 days.

(21) Appl. No.: 12/340,333

(22) Filed: Dec. 19, 2008

(65) Prior Publication Data

US 2009/0164091 A1 Jun. 25, 2009

(30) Foreign Application Priority Data

Dec. 20, 2007 (JP) ................... 2007-329109

(51) Int. Cl.
*G01N 27/419* (2006.01)
(52) U.S. Cl. ........ 204/424; 204/425; 204/426; 204/427; 205/783.5; 73/23.31; 73/23.32
(58) Field of Classification Search .......... 204/424–429; 73/23.31–23.32; 205/783.5–785
See application file for complete search history.

(56) References Cited

U.S. PATENT DOCUMENTS

| | | | | |
|---|---|---|---|---|
| 4,723,521 | A * | 2/1988 | Mieno et al. | ........ 123/682 |
| 6,228,252 | B1 | 5/2001 | Miyata | |
| 6,375,828 | B2 | 4/2002 | Ando | |
| 6,533,921 | B2 | 3/2003 | Miyata | |
| 6,743,352 | B2 | 6/2004 | Ando | |
| 6,923,902 | B2 | 8/2005 | Ando | |
| 7,438,791 | B2 * | 10/2008 | Sakayanagi | ............ 204/425 |
| 2001/0000598 | A1 * | 5/2001 | Miyata et al. | ......... 205/780.5 |
| 2003/0106808 | A1 | 6/2003 | Miyata | |

FOREIGN PATENT DOCUMENTS

| | | |
|---|---|---|
| JP | 62-198746 A | 9/1987 |
| JP | 10-288595 A | 10/1998 |
| JP | 11-14593 A | 1/1999 |
| JP | 11-148910 A | 6/1999 |
| JP | 2001-133429 A | 5/2001 |
| JP | 3589872 B2 | 8/2004 |

* cited by examiner

*Primary Examiner* — Keith Hendricks
*Assistant Examiner* — Bach Dinh
(74) *Attorney, Agent, or Firm* — Sughrue Mion, PLLC

(57) ABSTRACT

There is provided a control device for a gas sensor. The gas sensor is formed with first and second oxygen pumping cells to define first and second measurement chambers. Under the control of the sensor control device, the first and second oxygen pumping cells effect oxygen pumping actions against the first and second measurement chambers, respectively. The sensor control device is configured to detect currents through the first and second oxygen pumping cells, calculate a correction coefficient by comparison of a detection value of the first oxygen pumping cell current at a known oxygen concentration period with a previously stored reference value, correct the first oxygen pumping cell current by the correction coefficient and determine the concentration of nitrogen oxide in the gas under measurement based on the corrected first oxygen pumping cell current and the detected second oxygen pumping cell current.

3 Claims, 3 Drawing Sheets

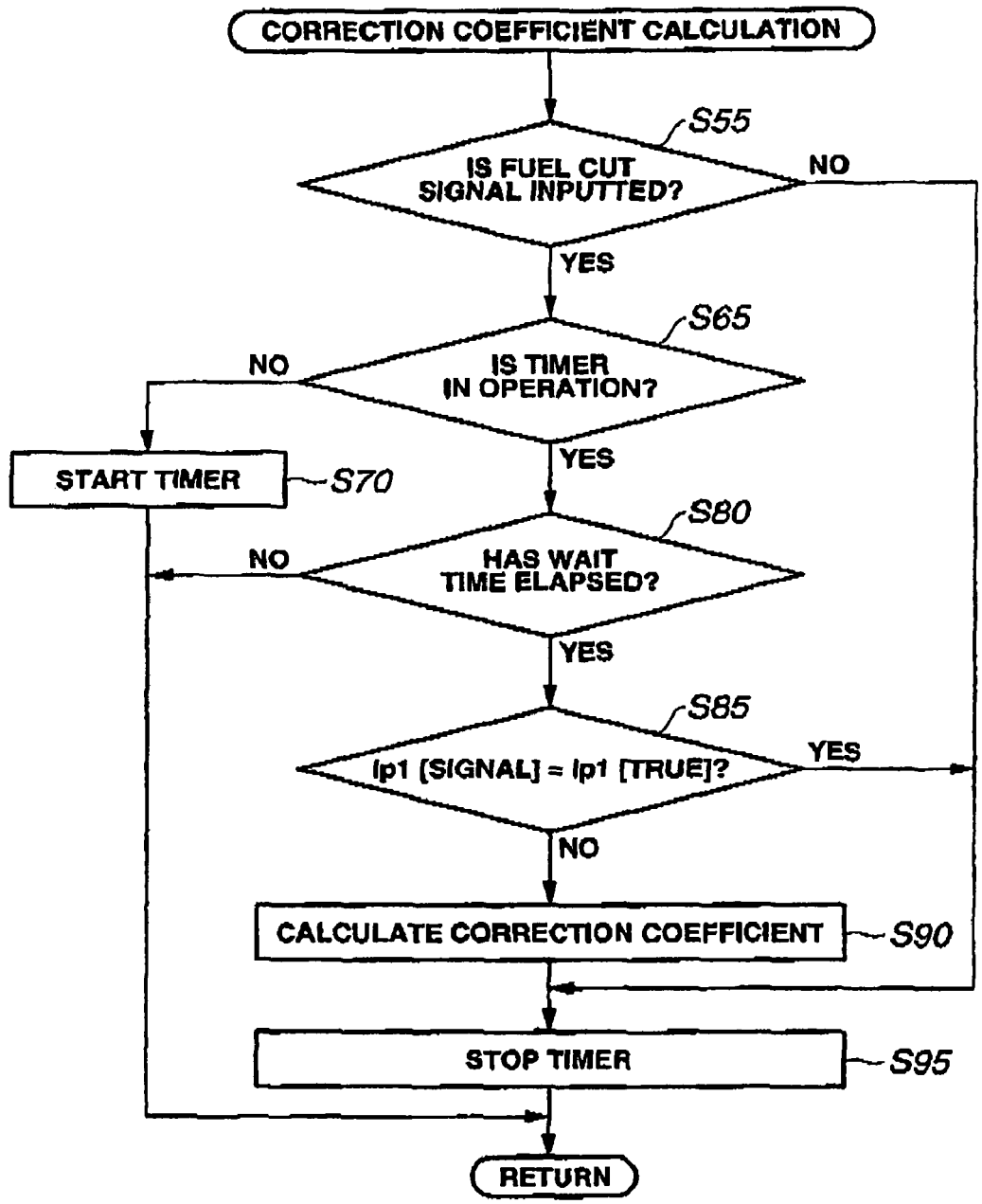

GAS SENSOR CONTROL DEVICE AND NITROGEN OXIDE CONCENTRATION DETECTION METHOD

BACKGROUND OF THE INVENTION

The present invention relates to a gas sensor control device for controlling a nitrogen oxide gas sensor and a nitrogen oxide Concentration detection method. Hereinafter, the term "front" refers to a gas sensing side with respect to the axial direction of a gas sensor and the term "rear" refer to a side opposite to the front side.

Japanese Laid-Open Patent Publication No. 10-288595 discloses a nitrogen oxide concentration detection apparatus consisting of a nitrogen oxide sensor and a sensor control device. The nitrogen oxide sensor includes a sensor element provided with a first oxygen pumping cell, a second oxygen pumping cell and an oxygen concentration measurement cell to define a first measurement chamber in communication with the outside atmosphere via a first diffusion rate control member and a second measurement chamber in communication with the first measurement chamber via a second diffusion rate control member. Each of the first oxygen pumping cell, the second oxygen pumping cell and the oxygen concentration detection cell has an oxygen ion conducting solid electrolyte layer and a pair of porous electrodes. The sensor control device detects a current developed between the porous electrodes of the second oxygen pumping cell by the oxygen pumping action during the application of a constant voltage to the second oxygen pumping cell, while supplying a current between the porous electrodes of the first oxygen pumping cell so as to keep the oxygen concentration of gas under measurement flowing from the first measurement chamber at a given level by the oxygen pumping action. The sensor control device further corrects for an offset in the detected second oxygen pumping cell current based on the first oxygen pumping cell current, and then, determines the concentration of nitrogen oxide (NOx) in the gas under measurement according to the corrected second oxygen pumping cell current. In this way, the nitrogen oxide concentration detection apparatus detects the NOx concentration of the gas under measurement using both of the first and second oxygen pumping cell currents.

In general, the nitrogen oxide sensor has a catalytic action to control or prevent the decomposition of NOx at the electrode surface. There thus arises a problem that the zero point of the nitrogen oxide sensor (i.e. the output point indicating that the concentration of a specific gas component in the gas under measurement is substantially zero) shifts as the catalytic activity of the nitrogen oxide sensor deteriorates during long-term use. In order to address such a zero point shift problem, Japanese Patent No. 3589872 and Japanese Laid-Open Patent Publication No. 2001-133429 propose sensor calibration techniques of adjusting the zero point of the nitrogen oxide sensor for high long-term detection accuracy.

SUMMARY OF THE INVENTION

When the sensor element deteriorates in performance during the long-term use, the first oxygen pumping cell current may not be detected properly and thus may contain an error. This results in a degradation of NOx concentration detection accuracy. The above-proposed sensor calibration techniques do not assume the case where the first oxygen pumping cell current contains an error caused by the sensor performance deterioration.

It is therefore an object of the present invention to provide a gas sensor control device capable of controlling a nitrogen oxide gas sensor properly without a degradation of detection accuracy even when the oxygen pumping cell current of the nitrogen oxide gas sensor cannot be detected properly due to a deterioration in sensor performance. It is also an object of the present invention to provide a nitrogen oxide concentration detection method.

According to a first aspect of the present invention, there is provided a control device for a gas sensor, the gas sensor comprising a sensor element formed with first and second oxygen pumping cells to define first and second measurement chambers in such a manner that gas under measurement first flows in the first measurement chamber via a first gas diffusion rate control member and then from the first measurement chamber into the second measurement chamber via a second gas diffusion rate control member, the first oxygen pumping cell having a pair of electrodes located inside and outside the first measurement chamber, the second oxygen pumping cell having a pair of electrodes located inside and outside the second measurement chamber, the control device being configured to: perform energization control of the first oxygen pumping cell so as to effect an oxygen pumping action of the first oxygen pumping cell against the first measurement chamber and thereby adjust the concentration of oxygen in the first measurement chamber to a given level; detect a first oxygen pumping cell current between the electrodes of the first oxygen pumping cell under the energization control of the first oxygen pumping cell; apply a voltage to the second oxygen pumping cell so as to control decomposition of nitrogen oxide in the gas under measurement in the second measurement chamber and effect an oxygen pumping action of the second oxygen pumping cell against the second measurement chamber; detect a second oxygen pumping cell current between the electrodes of the second oxygen pumping cell under the application of the voltage to the second oxygen pumping cell; read a detection value of the first oxygen pumping cell current at a known oxygen concentration period in which the gas under measurement is of known oxygen concentration; calculate a correction coefficient by comparison of the detection value with a previously stored reference value; correct the first oxygen pumping cell current by the correction coefficient; and determine the concentration of nitrogen oxide in the gas under measurement based on the corrected first oxygen pumping cell current and the detected second oxygen pumping cell current.

According to a second aspect of the present invention, there is provided a nitrogen oxide concentration detection method for detecting the concentration of nitrogen oxide in gas under measurement by means of a gas sensor, the gas sensor comprising a sensor element formed with first and second oxygen pumping cells to define first and second measurement chambers in such a manner that gas under measurement flows in the first measurement chamber via a first gas diffusion rate control member and then from the first measurement chamber into the second measurement chamber via a second gas diffusion rate control member, the first oxygen pumping cell having a pair of electrodes located inside and outside the first measurement chamber, the second oxygen pumping cell having a pair of electrodes located inside and outside the second measurement chamber, the nitrogen oxide concentration detection method comprising: performing energization control of the first oxygen pumping cell so as to effect an oxygen pumping action of the first oxygen pumping cell against the first measurement chamber and thereby adjust the concentration of oxygen in the first measurement chamber to a given level; detecting a first oxygen pumping cell current between the electrodes of the first oxygen pumping cell under the energization control of the first oxygen pumping cell; applying a voltage to the second oxygen pumping cell so as to control decomposition of nitrogen oxide in the gas under measurement in the second measurement chamber and effect an oxygen pumping action of the second oxygen pumping cell against the second measurement chamber; detecting a second oxygen pumping cell current between the electrodes of the second oxygen pumping cell under the application of the voltage to the second oxygen pumping cell; reading a detection value of the first oxygen pumping cell current at a known oxygen concentration period in which the gas under measurement is of known oxygen concentration; calculating a correction coefficient by comparison of the detection value with a previously stored reference value; correcting the first oxygen pumping cell current by the correction coefficient; and determining the concentration of nitrogen oxide in the gas under measurement based on the corrected first oxygen pumping cell current and the detected second oxygen pumping cell current.

The other objects and features of the present invention will also become understood from the following description.

BRIEF DESCRIPTION OF THE DRAWINGS

FIG. 3 is a flowchart for a correction coefficient calculation operation of the main operation process of the sensor control device according to one embodiment of the present invention.

DESCRIPTION OF THE EMBODIMENTS

A gas sensor system according to one embodiment of the present invention will be described below with reference to the drawings.

Figure 1:
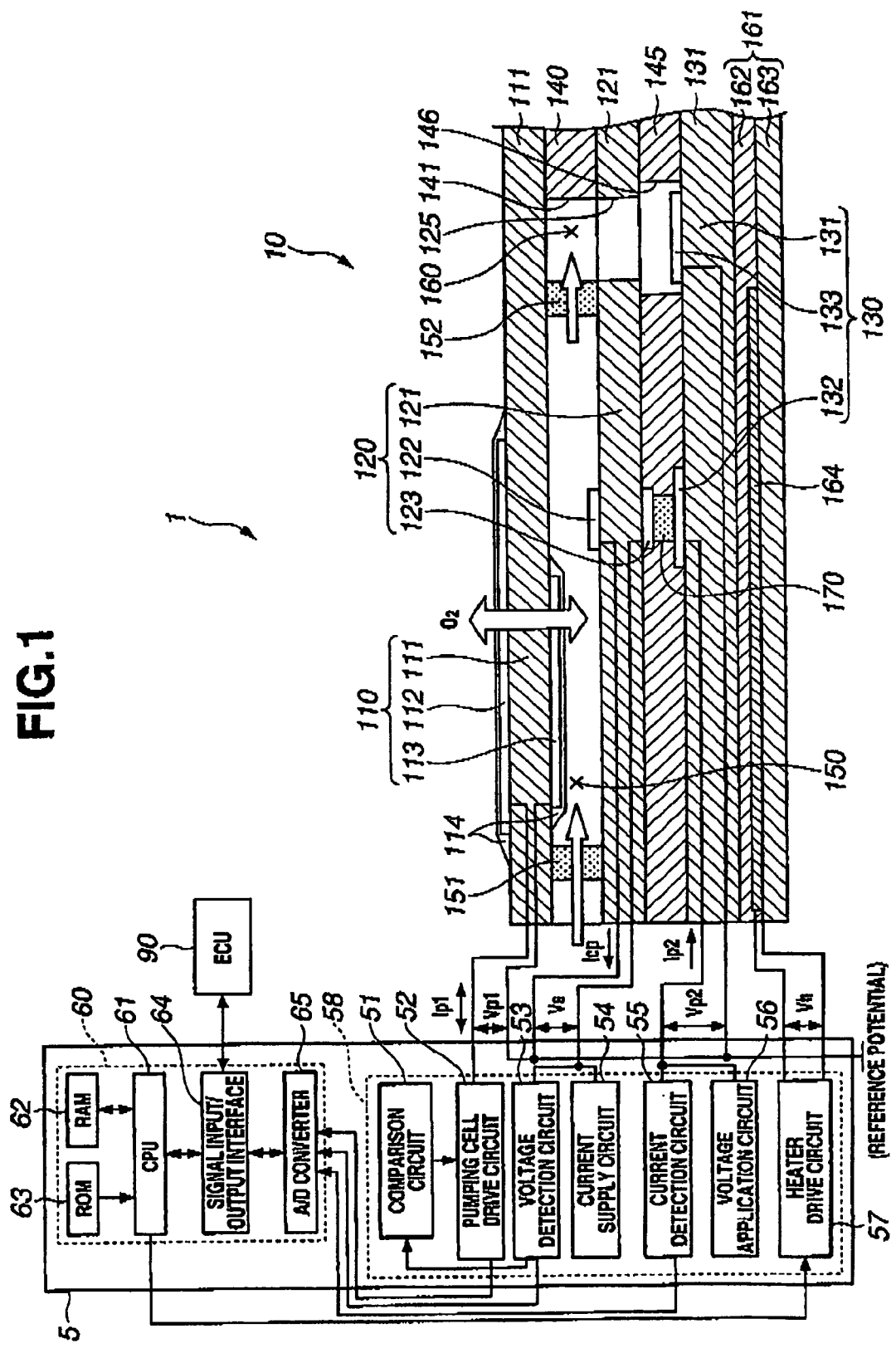
FIG. 1 is a schematic view of a gas sensor system equipped with a gas sensor and a sensor control device according to one embodiment of the present invention.
Figure 2:
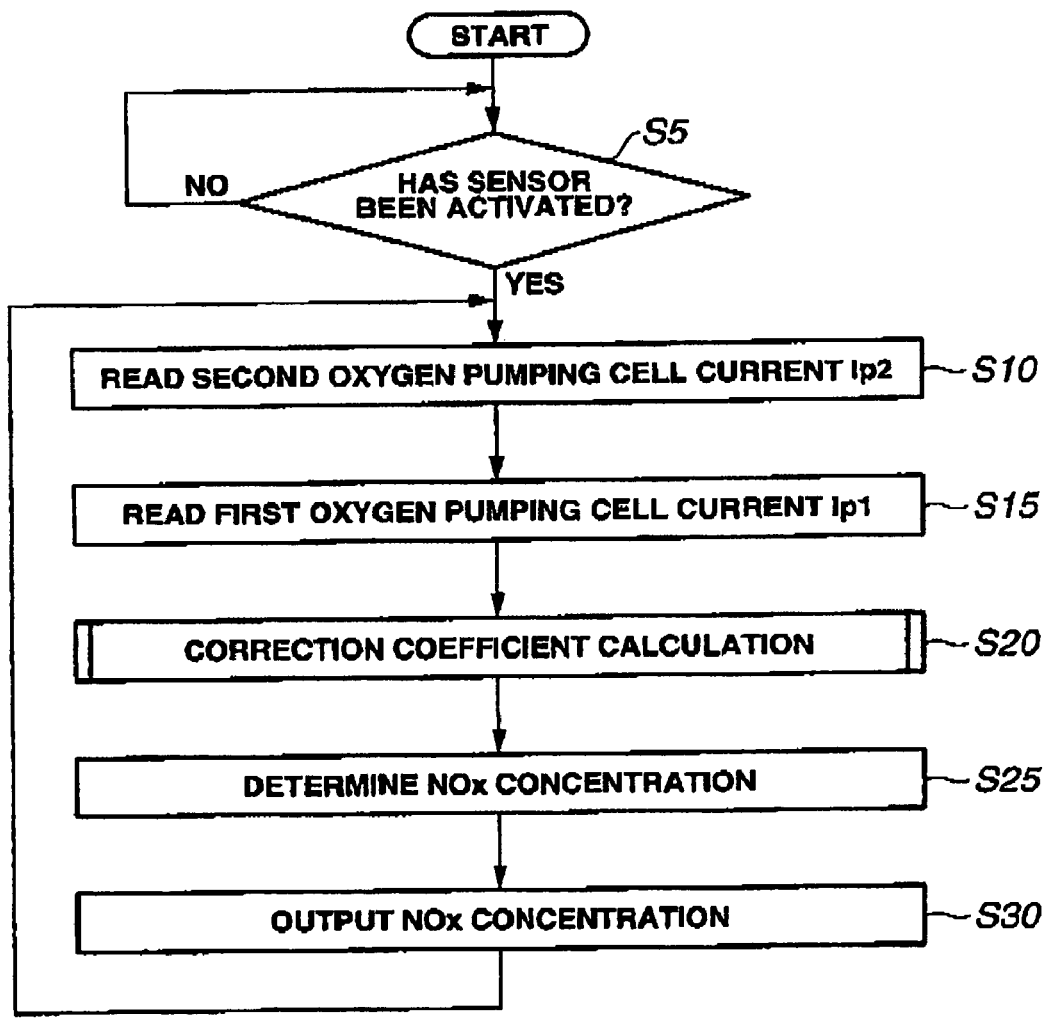
FIG. 2 is a flowchart for a main operation process of the sensor control device according to one embodiment of the present invention.

Referring to FIG. 1, the gas sensor system is equipped with a gas sensor 1 and a sensor control device 5.

The gas sensor 1 is a nitrogen oxide sensor, especially designed for use in an internal combustion engine, to measure the concentration of nitrogen oxide (NOx) in gas under measurement. In general, the gas sensor 1 includes an elongated, plate-shaped sensor element 10 for producing an output signal responsive to the NOx concentration of the gas under measurement, a housing for accommodating therein the sensor element 10 and mounting the gas sensor 1 on an exhaust passage of the engine so as to expose the sensor element 10 to exhaust gas, as the gas under measurement, inside the engine exhaust passage, signal wiring for taking the output signal from the sensor element 10 and a heater 161 for activating the sensor element 10 by heating.

The sensor element 10 has a laminated structure in which three plate-shaped solid electrolyte members 111, 121, and 131 are laminated to each other with an insulation sheet 140 interposed between the solid electrolyte members 111 and 121 and an insulation sheet 145 interposed between the solid electrolyte members 121 and 131. The solid electrolyte members 111, 121 and 131 are made of an oxygen ion conducting solid electrolyte material such as zirconia, whereas the insulation sheets 140 and 145 are predominantly composed of alumina.

As shown in FIG. 1, an opening 141, an opening 125 and an opening 146 are formed in the insulation sheet 140, the solid electrolyte member 121 and the insulation sheet 145, respectively, to define a first measurement chamber 150 between the solid electrolyte members 111 and 121 on a front side of the sensor element 10 and a second measurement chamber 160 between the solid electrolyte members 111 and 131 on a rear side of the sensor element 10. The first measurement chamber 150 is in communication with the engine exhaust passage (i.e. the outside atmosphere of the sensor element 10) via a first diffusion rate control member 151. The first diffusion rate control member 151 is located between the solid electrolyte members 111 and 121 at a front end of the first measurement chamber 150 so as to not only serve as a partition between the first measurement chamber 150 and the engine exhaust passage but control the rate of diffusion of the gas under measurement from the engine exhaust passage to the first measurement chamber 150 per unit of time. The second measurement chamber 160 is in communication with the first measurement chamber 150 via a second diffusion rate control member 152. The second diffusion rate control member 152 is located between the solid electrolyte members 111 and 121 at a rear end of the first measurement chamber 150 so as to not only serve as a partition between the first and second measurement chambers 150 and 160 but control the rate of diffusion of the gas under measurement from the first measurement chamber 150 to the second measurement chamber 160 per unit of time.

Another opening is also formed in the insulation sheet 145, as shown in FIG. 1, to define a reference oxygen chamber 170 between the solid electrolyte members 121 and 131. The reference oxygen chamber 170 is separated from the second measurement chamber 160 by the insulation sheet 145 and filled with a porous ceramic material.

The solid electrolyte member 111 is sandwiched between porous electrodes 112 and 113. The porous electrodes 112 and 113 are made of Pt, Pt alloy or Pt cermet (Pt/ceramic composite) and located at positions within the engine exhaust passage and the first measurement chamber 150 (i.e. outside and inside the first measurement chamber 150) on the opposite sides of the solid electrolyte member 111. By the passage of an electric current between the porous electrodes 112 and 113, the solid electrolyte member 111 allows oxygen ion conduction therethough between the engine exhaust passage and the first measurement chamber 150. The solid electrolyte member 111 and the porous electrodes 112 and 113 thus act together as a first oxygen pumping cell 110. Protection layers 114 are formed of porous ceramic material over the porous electrodes 112 and 113 to protect the porous electrodes 112 and 113 from any poisoning gas component (reducing gas component) in the gas under measurement.

The solid electrolyte member 121 is sandwiched between porous electrodes 122 and 123. The porous electrodes 122 and 123 are made of Pt, Pt alloy or Pt cermet (Pt/ceramic composite) and located at positions within the first measurement chamber 150 and the reference oxygen chamber 170 on the opposite sides of the solid electrolyte member 121, respectively. The solid electrolyte member 121 generates an electromotive force between the porous electrodes 122 and 123 according to a difference in oxygen partial pressures between the first measurement chamber 150 and the reference oxygen chamber 170. The solid electrolyte member 121 and the porous electrodes 122 and 123 thus act together as a partial pressure (oxygen concentration) measurement cell 120.

Further, porous electrodes 132 and 133 are provided on the side of the solid electrolyte member 131 facing the solid electrolyte member 121 at separate positions within the reference oxygen chamber 170 and the second measurement chamber 160 (i.e. outside and inside the second measurement chamber 160). These porous electrodes 132 and 133 are also made of Pt, Pt alloy or Pt cermet (Pt/ceramic composite). By the application of a voltage between the porous electrodes 132 and 133, the solid electrolyte member 131 allows oxygen ion conduction therethrough between the second measurement chamber 160 and the reference oxygen chamber 170. The solid electrolyte member 131 and the porous electrodes 132 and 133 thus act together as a second oxygen pumping cell 130.

As shown in FIG. 1, each of the porous electrode 113 inside the first measurement chamber 150, the porous electrode 122 inside the first measurement chamber 150 and the porous electrode 133 inside the second measurement chamber 160 is connected to a reference potential.

The heater 161 is disposed on the side of the solid electrolyte member 131 opposite from the insulation sheet 145 and has a heater pattern 164 embedded between two insulation sheets 162 and 163. The heater pattern 164 is made predominantly of Pt, whereas the insulation sheets 162 and 163 are predominantly made of alumina.

Referring again to FIG. 1, the sensor control device 5 includes a microcomputer 60 and an electric circuit module 58 electrically connected to the microcomputer 60 and to the signal wiring of the gas sensor 1.

The microcomputer 60 has a known configuration of a CPU 61, a RAM 62, a ROM 63, a signal input/output interface 64, an A/D converter 65 and a timer clock arranged to establish direct communications between the CPU 61 and the RAM 62 and ROM 63 and to establish communications between the CPU 61 and engine control unit (ECU) 90 via the signal input/output interface 64 and between the CPU 61 and the electric circuit module 58 via the signal input/output interface 64 and the A/D converter 65. The CPU 61 periodically receives a fuel cut signal, which is for disabling a fuel injection system to cut off fuel supply to the engine, as engine fuel supply information from the ECU 90. The CPU 61 also receives output signals from the electric circuit module 58. Based on these signals from the ECU 90 and the electric circuit module 58, the CPU 61 carries out processing operations to control the electric circuit module 58 and thereby operate the gas sensor 1. In the present embodiment, various programs and data such as a main processing program, a correction coefficient calculation program, an oxygen partial pressure detection program, a time update program, a reference current value Ip1[true], constants A and B and a sensor wait time are previously stored in the ROM 63 for the processing operations of the CPU 61 as will be explained later.

On the other hand, the electric circuit module 58 has a comparison circuit 51, a pumping cell drive circuit 52, a voltage detection circuit 53, a current supply circuit 54, a current detection circuit 55, a voltage application circuit 56 and a heater drive circuit 57.

The current supply circuit 54 supplies a weak current Icp between the porous electrodes 122 and 123 of the partial pressure measurement cell 120 (in the direction from the porous electrode 123 to the porous electrode 122) so that the partial pressure measurement cell 120 pumps oxygen from the first measurement chamber 150 to the reference oxygen chamber 170 through the solid electrolyte member 121.

The voltage detection circuit 53 detects a voltage (electromotive force) Vs between the porous electrodes 122 and 123 of the partial pressure measurement cell 120, and then, outputs the detected voltage Vs to the comparison circuit 51 and to the CPU 61.

The comparison circuit 51 compares the output voltage Vs of the partial pressure measurement cell 120 with a given reference voltage (e.g. 425 mV) and outputs the comparison result to the pumping cell drive circuit 52. This comparison result of the comparison circuit 51 is responsive to the oxygen partial pressure of the gas under measurement in the first measurement chamber 150.

The pumping cell drive circuit 52 supplies and regulates a current Ip1 between the porous electrodes 112 and 113 of the first oxygen pumping cell 110 depending on the comparison result of the comparison circuit 51 so as to keep the output voltage Vs of the partial pressure measurement cell 120 substantially constant at around the reference voltage. With this, the first oxygen pumping cell 110 pumps oxygen in and out of the first measurement chamber 150 through the solid electrolyte member 111 and thereby adjusts the concentration of oxygen in the first measurement chamber 150 to a given level (e.g. $10^{-8}$ to $10^{-9}$ atm). More specifically, in the case where the oxygen concentration of the first measurement chamber 150 is lower than the given level, the pumping cell drive circuit 52 supplies the current Ip1 through the first oxygen pumping cell 110 in the direction that the porous electrode 112 serves as a negative electrode so that the first oxygen pumping cell 110 pumps oxygen into the first measurement chamber 150 and thereby increases the oxygen concentration of the first measurement chamber 150 to the given level. In the case where the oxygen concentration of the first measurement chamber 150 is higher than the given level, by contrast, the pumping cell drive circuit 52 supplies the current Ip1 through the first oxygen pumping cell 110 in the direction that the porous electrode 113 serves as a negative electrode so that the first oxygen pumping cell 110 pumps oxygen out from the first measurement chamber 150 and thereby decreases the oxygen concentration of the first measurement chamber 150 to the given level. Namely, the pumping cell drive circuit 52 performs energization control on the first oxygen pumping cell 110 to control the direction and intensity of the first oxygen pumping cell current Ip1 depending on the oxygen concentration of the gas under measurement. The pumping cell drive circuit 52 also outputs the first oxygen pumping cell current Ip1 to the CPU 61.

The voltage application circuit 56 applies a voltage Vp2 (e.g. 450 mV) between the porous electrodes 132 and 133 of the second oxygen pumping cell 130 so that the second oxygen pumping cell 130 pumps oxygen from the second measurement chamber 160 to the reference oxygen chamber 170 through the solid electrolyte member 131.

The current detection circuit 55 detects a current Ip2 between the porous electrodes 132 and 133 of the second oxygen pumping cell 130 and outputs the detected second oxygen pumping cell current Ip2 to the CPU 61.

The heater drive circuit 57 supplies a current to the heater pattern 164 of the heater 161 and thereby drives the heater pattern 164. As the heater pattern 164 is in the form of a single continuous electrode pattern having one end grounded and the other end connected to the heater drive circuit 57, the heater drive circuit 57 performs PWM (pulse width modulation) energization control of the heater pattern 164 in such a manner as to heat and maintain the solid electrolyte members 111, 121 and 131 (sensor element 10) at a given activation temperature in the present embodiment.

The above-structured gas sensor system operates as follows.

Upon the energization of the heater pattern 164 by the heater drive circuit 57, the heater pattern 164 activates the solid electrolyte members 111, 121 and 131 by heating. When the engine exhaust gas is introduced from the engine exhaust passage into the first measurement chamber 150 through the diffusion rate control member 151, the current supply circuit 54 supplies the current Icp between the porous electrodes 122 and 123. With the supply of the current Icp, the partial pressure measurement cell 120 effects its oxygen pumping action to ionize $O_2$ in the exhaust gas at the porous electrode 122 inside the first measurement chamber 150 and conduct the resulting oxygen ions through the solid electrolyte member 121 to the reference oxygen chamber 170. At this time, the voltage detection circuit 53 detects the voltage Vs between the porous electrodes 122 and 123 and outputs the detected voltage Vs to the comparison circuit 51. The comparison circuit 51 compares the detected voltage Vs with the given reference voltage and outputs the comparison result to the pumping cell drive circuit 52. The pumping cell drive circuit 52 supplies the current Ip1 between the porous electrodes 112 and 113 in accordance with the comparison result of the comparison circuit 51. With the supply of the current Ip1, the first oxygen pumping cell 110 effects its oxygen pumping action against the first measurement chamber 150 to adjust the oxygen concentration of the exhaust gas in the first measurement chamber 150 to the given level. The pumping cell drive circuit 52 also detects and outputs the first oxygen pumping cell current Ip1 to the CPU 61. After the oxygen concentration of the exhaust gas in the first measurement chamber 150 is controlled to the given level, the exhaust gas is fed from the first measurement chamber 150 into the second measurement chamber 160 through the diffusion rate control member 152. Upon contact of NOx in the exhaust gas with the porous electrode 133 inside the second measurement chamber 160, the NOx gets decomposed (reduced) into $N_2$ and $O_2$ by the catalytic action of the porous electrode 133. The voltage application circuit 56 then applies the voltage Vp2 between the porous electrodes 132 and 133. With the application of the voltage Vp2, the second oxygen pumping cell 130 effects its oxygen pumping action against the second measurement chamber 160 to ionize the dissociated $O_2$ in the second measurement chamber 160 and conduct the resulting oxygen ions through the solid electrolyte member 131 to the reference oxygen chamber 170. The current detection circuit 55 detects the current Ip2 between the porous electrodes 132 and 133 and outputs the detected second oxygen pumping cell current Ip2 to the CPU 61. Finally, the CPU 61 determines the NOx concentration of the exhaust gas based on the output signals Ip1 and Ip2 from the pumping cell drive circuit 52 and the current detection circuit 55.

Herein, the given level of oxygen remains in the first measurement chamber 150 without being pumped out from the first measurement chamber 150 even by the oxygen pumping action of the first oxygen pumping cell 110. This residual oxygen flows together with NOx in the exhaust gas from the first measurement chamber 150 into the second measurement chamber 160 and gets ionized and conducted by the second oxygen pumping cell 130. The second oxygen pumping cell current Ip2 is thus given as the sum of a current value associated with the NOx in the exhaust gas and an offset associated with the residual oxygen in the exhaust gas in the first measurement chamber 150.

If the CPU 61 determines the NOx concentration of the exhaust gas based only on the second oxygen pumping cell current Ip2, the NOx concentration determination result of the CPU 61 contains an error caused by the offset of the second oxygen pumping cell current Ip2. This leads to a degradation of NOx concentration determination accuracy. In order to prevent such a degradation of NOx concentration determination accuracy, it is conceivable to determine the NOx concentration of the exhaust gas according to the following equation (1) by canceling out the offset of the second oxygen pumping cell current Ip2 by the first oxygen pumping cell current Ip1:

$$\text{NOx concentration [ppm]} = A \times Ip2 + B \times Ip1 \quad (1)$$

where A and B are the constants specific to the sensor element 10.

The first oxygen pumping cell current Ip1 may not however be detected properly corresponding to the residual oxygen concentration of the exhaust gas in the first measurement chamber 150 when the sensor element 10 deteriorates in performance during the long-term use. In such a case, the CPU 61 cannot properly cancel out the offset of the second oxygen pumping cell current Ip2 by the first oxygen pumping cell current Ip1 and causes an accuracy degradation in the NOx concentration determination result.

The CPU 61 is accordingly configured to, when an error occurs in the first oxygen pumping cell current Ip1 due to a performance deterioration of the sensor element 10, correct such an error in the first oxygen pumping cell current Ip1 in the present embodiment. More specifically, the CPU 61 first reads a value of the first oxygen pumping cell current Ip1 at a known oxygen concentration period as a detection value Ip1[signal] and calculates a correction coefficient C from the detection value Ip1[signal] and the previously stored reference value Ip1[true] according to the following equation (2).

$$C = Ip1[\text{true}] / Ip1[\text{signal}] \quad (2)$$

The CPU 61 then correct the first oxygen pumping cell current Ip1 by the correction coefficient C, corrects the second oxygen pumping cell current Ip2 by the corrected first oxygen pumping cell current Ip1 and determines the NOx concentration of the exhaust gas based on the corrected second oxygen pumping cell current Ip2 according to the following equation (3):

$$\text{NOx concentration [ppm]} = A \times Ip2 + B \times C \times Ip1 \quad (3)$$

where A and B are the constants specific to the sensor element 10; and C is the correction coefficient.

The equations (2) and (3) can be modified depending on the characteristics of the gas sensor 1 (sensor element 10). Although the CPU 61 makes correction of the first oxygen pumping cell current Ip1, correction of the second oxygen pumping cell current Ip2 and determination of the NOx concentration simultaneously in the equation (3), the CPU 61 may alternatively make correction of the first oxygen pumping cell current Ip1, correction of the second oxygen pumping cell current Ip2 and determination of the NOx concentration individually in sequence.

The known oxygen concentration period is defined as a period of time in which the gas under measurement (i.e. the ambient atmosphere of the sensor element 10) has a stable, known oxygen concentration by replacement of the exhaust gas with the atmospheric air of known oxygen concentration. In the present embodiment, for example, the CPU 61 decides on the known oxygen concentration period upon the assumption that the exhaust gas would be replaced with the atmospheric air at the time when there is continuous, periodical input of the fuel cut signal from ECU 90 for a predetermined wait time. By setting the known oxygen concentration period as the fuel cut period, the correction coefficient C can be easily calculated by using, as the detection value Ip1[signal], the reading of the first oxygen pumping cell current Ip1 in a state of the sensor element 10 is exposed to the atmospheric air as the gas under measurement. The known oxygen concentration period is not limited to the above fuel cut period. In the case where the ambient atmosphere of the sensor element 10 is charged with the air of known oxygen concentration immediately after the receipt of the fuel cut signal, the CPU 61 way decide on the known oxygen concentration period at the time of receipt of the fuel cut signal. In the case where the gas sensor 1 has equipment to supply any gas of known oxygen concentration as calibration gas to the sensor element 10, the known oxygen concentration period can alternatively be defined as a period of time in which the ambient atmosphere of the sensor element 10 is charged with the calibration gas.

By the above correction of the first oxygen pumping cell current Ip1, it is possible to cancel out an offset of the second oxygen pumping cell current Ip2 associated with the residual oxygen in the first measurement chamber 150 more appropriately and maintain high accuracy of NOx concentration determination even when the first oxygen pumping cell current Ip1 does not represent a proper, correct value due to a performance deterioration of the sensor element 10.

In the present embodiment, the CPU 61 determines the NOx concentration of the exhaust gas by the execution of the main processing program. Separately from the main processing program, the CPU 61 executes the oxygen partial pressure detection program to detect the oxygen partial pressure of the gas under measurement in the first measurement chamber 150 based on the potential difference between the porous electrodes 122 and 123 of the partial pressure measurement cell 120 by means of the comparison circuit 51. Further, the pumping cell drive circuit 52 operates independently to energize the first oxygen pumping cell 110 according to the oxygen partial pressure in such a manner that the first oxygen pumping cell 110 keeps the oxygen concentration of the gas under measurement in the first measurement chamber 150 at the given constant level by the oxygen pumping action. The voltage application circuit 56 also operates independently to apply the voltage Vp2 to the second oxygen pumping cell 130 in such a manner that the second oxygen pumping cell 130 controls the decomposition of NOx in the gas under measurement within the second measurement chamber 160 and pumps the dissociated $O_2$ from the second measurement chamber 160 by the oxygen pumping action.

Upon initiation of the main processing program, the CPU 61 first judges at step S5 whether the sensor element 10 has been activated. There is no particular restriction on how to judge the activation state of the sensor element 10. For example, the CPU 61 may judge the activation state of the sensor element 10 by checking whether a predetermined time period has elapsed from the initiation of energization of the heater pattern 164 or by checking whether the temperature (or temperature-correlated internal resistance) of the solid electrolyte member 111, 121, 131 has reached the given level. The temperature (internal resistance) of the solid electrolyte member 111, 121, 131 can be detected by any known technique (means). If Yes at step S5, the CPU 61 proceeds to steps S10 and S15. If No at step S5, the CPU 61 repeats step S5 until the sensor element 10 is judged as being activated.

At step S10, the CPU 61 reads the second oxygen pumping cell current Ip2 from the current detection circuit 55 and stores the second oxygen pumping cell current Ip2 in the RAM 62.

At step S15, the CPU 61 reads the first oxygen pumping cell current Ip1 from the pumping cell drive circuit 52 and stores the first oxygen pumping cell current Ip1 as the detection value Ip1[signal] in the RAM 62.

At step S20, the CPU 61 executes the correction coefficient calculation program to calculate the correction coefficient C for canceling out an error caused in the first oxygen pumping cell current Ip1 by a deterioration of the sensor element 10. The correction coefficient calculation program goes through the following stops as shown in FIG. 3.

At step S55, the CPU 61 judges whether there is input of the fuel cut signal from the ECU 90. As the CPU 61 stores the fuel cut signal in the RAM 62 upon receipt thereof under another separately executed program, the CPU 61 judges the presence or absence of input of the fuel cut signal from the ECU 90 by checking whether the latest fuel cut signal has been stored in the RAM 62. If No at step S55, the CPU 61 proceeds to step S95. If Yes at step S55, the CPU 61 proceeds to step S65.

At step S65, the CPU 61 judges whether the timer clock is in operation (i.e. the time update program is in execution). In the present embodiment, the CPU 61 operates the timer clock by execution of the time update program so as to update the timer count periodically during the continuous input of the fuel cut signal and to store the timer count in RAM 62. The timer count is thus larger than its initial value (0) when the timer is in operation and is set to 0 when the timer is not in operation. If No at step S65, the CPU 61 proceeds to step S70. If Yes at step S65, the CPU 61 proceeds to step S80.

At step S70, the CPU 61 initiates the time update program and starts the timer.

At step S80, the CPU 61 retrieves the timer count from the RAM 62 and judges whether the timer count reaches the predetermined wait time. This operation step makes it possible to accurately decide on whether the sensor element 10 is in the known oxygen concentration period without any additional configuration. If No at step S80, the CPU 61 exits from the correction coefficient calculation program and returns to the main processing program. If Yes at step S80, the CPU 61 proceeds to step S85.

At step S85, the CPU 61 retrieves the first oxygen pumping cell current detection value Ip1[signal] and the reference value Ip1[true] from the RAM 62 and the ROM 63, respectively, compares the detection value Ip1[signal] with the reference value Ip1[true] and judges whether the detection value Ip1[signal] agrees with the reference value Ip1[true]. If No at step S85, the CPU 61 proceeds to step S90. If Yes at step S85, the CPU 61 proceeds to step S95.

At step S90, the CPU 61 calculates the correction coefficient C according to the equation (2) and stores the calculated correction coefficient C in the RAM 62. The CPU 61 then proceeds to step S95.

At step S95, the CPU 61 resets the timer count to 0 and finishes the time update program to stop the timer. After that, the CPU 61 returns to the main processing program upon exit from the correction coefficient calculation program.

At step S25, the CPU 61 retrieves the first and second oxygen pumping cell currents Ip1 and Ip2 and the correction coefficient C from tee RAM 62 and, at the same time, retrieves the constants A and B from the ROM 63. Then, the CPU 61 determines the NOx concentration of the exhaust gas according to the equation (3) and stores the NOx concentration determination result in the RAM 62. In the case where the correction coefficient C is not stored in the RAM 62, the CPU 61 sets the correction coefficient C to its initial value (1) stored in the RAM 62.

At step S30, the CPU 61 outputs the NOx concentration determination result to the ECU 90 for engine air-fuel ratio feedback control etc. The CPU 61 returns to step S10.

The above nitrogen oxide concentration process is carried out repeatedly until the sensor control device 5 is powered off.

As described above, the sensor control device 5 is configured to read the value of the first oxygen pumping cell current Ip1 at the known oxygen concentration period as the detection value Ip1[signal], calculate the correction coefficient C by division of the previously stored reference value Ip1[true] by the oxygen pumping cell current detection value Ip1[signal], correct the first oxygen pumping cell current Ip1 by the correction coefficient C and determine the NOx concentration based on the corrected first oxygen pumping cell current Ip1 and the detected second oxygen pumping cell current Ip2 when the oxygen pumping cell current Ip1 cannot be detected properly due to a performance deterioration in the sensor element 10. It is possible for the sensor control device 5 to compensate for such a performance deterioration in the sensor element 10 appropriately and maintain high NOx concentration determination accuracy during long-term use.

The entire contents of Japanese Patent Application No. 2007-329109 (filed on Dec. 20, 2007) are herein incorporated by reference.

Although the present invention has been described with reference to the above embodiment, the invention is not limited to this exemplary embodiment. Various modification and variation of the embodiment described above will occur to those skilled in the art in light of the above teachings.

The configurations of the gas sensor 1 and the sensor element 10 can be modified appropriately. For example, the gas sensor 1 (sensor element 10) may have no partial pressure measurement cell 120 although the partial pressure measurement cell 120 is provided below the first measurement chamber 150 in the gas sensor 1 (sensor element 10) in the above exemplary embodiment. In this case, the sensor control device 5 could be modified to regulate the voltage between the porous electrodes 112 and 113 of the first oxygen pumping cell 110 based on the first oxygen pumping cell current Ip1 and control the first oxygen pumping cell 110 to keep the oxygen concentration in the first measurement chamber 150 at the given level.

The timing of calculation of the correction coefficient C is not particularly limited. Although the correction coefficient C is calculated at step S90 every time the sensor element 10 is judged as being exposed to the air of known oxygen concentration at step S80 and the necessity for calculation of the correction coefficient C is confirmed at step S85 in the above exemplary embodiment, the calculation of the correction coefficient C may be omitted after being repeated a predetermined number of times during a predetermined time period (e.g. 1 drive). The correction coefficient C may alternatively be calculated, subsequent to judging the sensor element 10 as being exposed to the air of known oxygen concentration, without confirming the necessity for calculation of the correction coefficient C.

The oxygen pumping actions of the first and second oxygen pumping cells 110 and 130 may alternatively be effected under the control of the CPU 61 although the oxygen pumping actions of the oxygen pumping cells 110 and 130 are effected under the control of the pumping cell drive circuit 52 and the voltage application circuit 56, respectively, in the above exemplary embodiment. Further, a dedicated circuit or circuits may be provided to carry out some or the whole of the processing operations of the CPU 61.

Any known technique of correction of residual oxygen associated offset current may additionally be applied to the above NOx concentration determination process.

The scope of the invention is defined with reference to the following claims.

What is claimed is:

1. A control device for a gas sensor, the gas sensor comprising a sensor element formed with first and second oxygen pumping cells to define first and second measurement chambers in such a manner that gas under measurement first flows in the first measurement chamber via a first gas diffusion rate control member and then from the first measurement chamber into the second measurement chamber via a second gas diffusion rate control member, the first oxygen pumping cell having a pair of electrodes located inside and outside the first measurement chamber, the second oxygen pumping cell having a pair of electrodes located inside and outside the second measurement chamber, the gas chamber being mounted on an exhaust passage of an internal combustion engine such that the sensor element is exposed to the inside of the exhaust passage, the control device being configured to:

perform energization control of the first oxygen pumping cell so as to effect an oxygen pumping action of the first oxygen pumping cell against the first measurement chamber and thereby adjust the concentration of oxygen in the first measurement chamber to a given level;

detect a first oxygen pumping cell current between the electrodes of the first oxygen pumping cell under the energization control of the first oxygen pumping cell;

apply a voltage to the second oxygen pumping cell so as to control decomposition of nitrogen oxide in the gas under measurement in the second measurement chamber and effect an oxygen pumping action of the second oxygen pumping cell against the second measurement chamber;

detect a second oxygen pumping cell current between the electrodes of the second oxygen pumping cell under the application of the voltage to the second oxygen pumping cell;

read a detection value of the first oxygen pumping cell current at every fuel cut period in which a supply of fuel to the engine is stopped;

calculate, at every fuel cut period, a correction coefficient for cancelling out error in the first oxygen pumping cell current caused by deterioration of the sensor element by comparison of the detection value with a previously stored reference value in accordance with the following equation (2):

$$C = Ip1[\text{true}]/Ip1[\text{signal}] \tag{2},$$

wherein C is the correction coefficient, Ip1[signal] is the detection value, and Ip1[true] is the previously stored reference value;

correct the first oxygen pumping cell current by the correction coefficient every time the correction coefficient is calculated to yield a corrected first oxygen pumping cell current;

correct the second oxygen pumping cell current by the corrected first oxygen pumping cell current to thereby yield a corrected second oxygen pumping cell current; and determine the concentration of nitrogen oxide in the gas under measurement based on the corrected first oxygen pumping cell current and the corrected second oxygen pumping cell current in accordance with the following equation (3):

$$\text{NOx concentration [ppm]} = A \times Ip2 + B \times C \times Ip1 \tag{3},$$

wherein A and B are constants specific to the sensor element, C is the correction coefficient, Ip1 is the corrected first oxygen pumping cell current and Ip2 is the corrected second oxygen pumping cell current.

2. The control device according to claim 1, wherein the control device is provided separately from an engine control unit and is equipped with a signal input/output interface to output a signal indicative of the determined nitrogen oxide concentration to the engine control unit.

3. A nitrogen oxide concentration detection method for detecting the concentration of nitrogen oxide in gas under measurement by means of a gas sensor, the gas sensor comprising a sensor element formed with first and second oxygen pumping cells to define first and second measurement chambers in such a manner that gas under measurement flows in the first measurement chamber via a first gas diffusion rate control member and then from the first measurement chamber into the second measurement chamber via a second gas diffusion rate control member, the first oxygen pumping cell having a pair of electrodes located inside and outside the first measurement chamber, the second oxygen pumping cell having a pair of electrodes located inside and outside the second measurement chamber, the gas sensor being mounted on an exhaust passage of an internal combustion engine such that the sensor element is exposed to the inside of the exhaust passage, the nitrogen oxide concentration detection method comprising:

performing energization control of the first oxygen pumping cell so as to effect an oxygen pumping action of the first oxygen pumping cell against the first measurement chamber and thereby adjust the concentration of oxygen in the first measurement chamber to a given level;

detecting a first oxygen pumping cell current between the electrodes of the first oxygen pumping cell under the energization control of the first oxygen pumping cell;

applying a voltage to the second oxygen pumping cell so as to control decomposition of nitrogen oxide in the gas under measurement in the second measurement chamber and effect an oxygen pumping action of the second oxygen pumping cell against the second measurement chamber;

detecting a second oxygen pumping cell current between the electrodes of the second oxygen pumping cell under the application of the voltage to the second oxygen pumping cell;

reading a detection value of the first oxygen pumping cell current at every fuel cut period in which a supply of fuel to the engine is stopped;

calculating, at every fuel cut period, a correction coefficient for cancelling out error in the first oxygen pumping cell current caused by deterioration of the sensor element by comparison of the detection value with a previously stored reference value in accordance with the following equation (2):

$$C = Ip1[\text{true}]/Ip1[\text{signal}] \qquad (2),$$

wherein C is the correction coefficient, Ip1[signal] is the detection value, and Ip1[true] is the previously stored reference value;

correcting the first oxygen pumping cell current by the correction coefficient every time the correction coefficient is calculated to yield a corrected first oxygen pumping cell current;

correcting the second oxygen pumping cell current by the corrected first oxygen pumping cell current to thereby yield a corrected second oxygen pumping cell current; and determining the concentration of nitrogen oxide in the gas under measurement based on the corrected first oxygen pumping cell current and the corrected second oxygen pumping cell current in accordance with the following equation (3):

$$\text{NOx concentration [ppm]} = A \times Ip2 + B \times C \times Ip1 \qquad (3),$$

wherein A and B are constants specific to the sensor element, C is the correction coefficient, Ip1 is the corrected first oxygen pumping cell current and Ip2 is the corrected second oxygen pumping cell current.

* * * * *